US008450518B2

(12) United States Patent
Deng et al.

(10) Patent No.: US 8,450,518 B2
(45) Date of Patent: May 28, 2013

(54) METHOD FOR PREPARING A CARBAMATE, A CATALYST APPLIED IN THE METHOD, A METHOD FOR PREPARING THE CATALYST AND USE THEREOF

(75) Inventors: Youquan Deng, Gansu (CN); Liguo Wang, Gansu (CN); Yubo Ma, Gansu (CN); Xiaoguang Guo, Gansu (CN); Stefan Wershofen, Mönchengladbach (DE); Stephan Klein, Shanghai (CN); Hongchao Li, Pudong (CN)

(73) Assignee: Bayer MaterialScience AG, Leverkusen (DE)

( * ) Notice: Subject to any disclaimer, the term of this patent is extended or adjusted under 35 U.S.C. 154(b) by 376 days.

(21) Appl. No.: 12/758,064

(22) Filed: Apr. 12, 2010

(65) Prior Publication Data

US 2010/0274041 A1 Oct. 28, 2010

(30) Foreign Application Priority Data

Apr. 14, 2009 (CN) .......................... 2009 1 0049244

(51) Int. Cl.
*C07C 269/00* (2006.01)
(52) U.S. Cl.
USPC ........................................................ 560/115
(58) Field of Classification Search
None
See application file for complete search history.

(56) References Cited

U.S. PATENT DOCUMENTS

| | | | |
|---|---|---|---|
| 2,837,561 A | 6/1958 | Beinfest et al. | |
| 3,013,064 A | 12/1961 | Beinfest et al. | |
| 3,554,730 A | 1/1971 | Slater et al. | |
| 3,574,711 A | 4/1971 | Robeson | |
| 4,242,520 A | 12/1980 | Moy | |
| 4,276,195 A * | 6/1981 | Verkade | 502/155 |
| 5,194,660 A * | 3/1993 | Leung et al. | 560/24 |
| 6,399,808 B1 | 6/2002 | Jung | |

FOREIGN PATENT DOCUMENTS

| | | |
|---|---|---|
| CN | 1365969 A | 8/2002 |
| CN | 1475481 A | 2/2004 |

OTHER PUBLICATIONS

Yoshida, Yasuhiko et al, Novel Synthesis of Carbamate Ester from Carbon Dioxide, Amines and Alkyl Halides, Bull. Chem. Soc. Jpn., vol. 62, No. 5, 1989, pp. 1534-1538.

* cited by examiner

*Primary Examiner* — Yevegeny Valenrod
(74) *Attorney, Agent, or Firm* — N. Denise Brown

(57) ABSTRACT

The present invention pertains to a novel method for preparing a carbamate, in which the method comprises reacting an aliphatic substituted urea and/or its derivatives, with a hydroxyl group containing compound to obtain a carbamate. In addition, the present invention provides a novel catalyst which is suitable for catalyzing the reaction to form a carbamate, and a method for preparing the novel catalyst. The method of the present invention for preparing a carbamate does not involve the application of carbon monoxide which is toxic, and the reaction conditions are relatively mild with high catalytic activity, high reaction selectivity of the catalyst, and a relatively short reaction time. Furthermore, the catalyst is separated from the reaction system and reused easily, which will facilitates scale up and industrial application.

9 Claims, No Drawings

US 8,450,518 B2

METHOD FOR PREPARING A CARBAMATE, A CATALYST APPLIED IN THE METHOD, A METHOD FOR PREPARING THE CATALYST AND USE THEREOF

CROSS REFERENCE TO RELATED PATENT APPLICATION

The present patent application claims the right of priority under 35 U.S.C. §119 (a)-(d) of Chinese Patent Application No. 200910049244.8, filed on Apr. 14, 2009.

BACKGROUND OF THE INVENTION

The present invention pertains to the synthesis of a carbamate, especially relates to a new method for preparing a carbamate, a catalyst applied in the method, a method for preparing the catalyst and use thereof.

Carbamate is a kind of chemical intermediate that is widely used for preparing various chemical products. For example, methyl carbamates are not only suitable for the preparation of melamine derivatives and polyethylenamine, but they can also be reacted with unsaturated hydrocarbons, aldehydes, ketones, polyols or aromatics to obtain various derivatives. In addition, ethyl carbamate can be used to prepare a kind of promising ataractic, alkanediol dicarbamates (Sidney Beinfest etc, preparation of organic mono-carbamates, U.S. Pat. No. 2,837,561). Furthermore, butyl carbamate can be reacted with formaldehyde to obtain hydroxymethyl derivatives, which can be used as an anti-creasing reagent for textile materials (Max Robeson etc. production of alkyl carbamate, U.S. Pat. No. 3,574,711). Moreover, carbamates are also suitable for preparing the corresponding organic carbonates, or as new carbonylation reagents to prepare isocyanates.

Due to the wide use of carbamates, the method for preparing the same has attracted much attention. U.S. Pat. No. 4,242,520 discloses a method for preparing carbamates by reacting an amine, carbon monoxide (i.e. CO) and a hydroxyl compound in the presence of a catalyst. However, carbon monoxide may potentially harm the health of producers or users, because it is a toxic gas.

Moreover, it was reported that carbon dioxide ($CO_2$) can be used as a carbonylation reagent to replace toxic carbon monoxide in the preparation of organic carbonates (Yoshida, Y., et al., Bull. Chem. Soc. Japan 1989, 62, 1534), in which, $CO_2$ was directly or indirectly applied. For example, U.S. Pat. No. 6,399,808 discloses a method to form organic carbamates by reacting an amine and $CO_2$ in the presence of an organic electrophilic reagent. This method, however, required an anhydrous solvent, and halogenide salts were simultaneously formed with the organic carbamates.

In addition, the urea alcoholysis method was also a mature method widely applied to prepare carbamates. In this method, carbamates are obtained by reacting urea and a hydroxyl group containing compound under proper conditions, wherein CO was avoided during the production. The method can be used under the condition of using a catalyst. Suitable catalysts include zinc oxide as disclosed in U.S. Pat. No. 3,574,711; copper acetate as disclosed in U.S. Pat. Nos. 2,837,561 and 3,013,064; composites of transition metal oxides and acids as disclosed in U.S. Pat. No. 3,554,730; nano-$TiO_2$ and $R_3N$ catalyst systems as disclosed in CN 1365969; and metal oxides such as ZnO, MgO, CaO, $Pb_2O_3$ etc. as disclosed in CN 1475481. However, the various catalysts disclosed above were not perfect when used in urea alcoholysis methods. One problem is that the carbamate yields were not high. Also, the catalyst was difficult to separate from the reaction products such that it could be recycled.

It is therefore necessary, from an industrial point of view, to develop a new method for preparing carbamates and a new catalyst for the method. It would be desirable for the method to prepare carbamates by reacting substituted urea and hydroxyl groups containing compounds, while allowing for the catalyst to be easily separated and recycled.

SUMMARY OF THE INVENTION

The objective of this invention is to provide a novel method for the preparation of a carbamate. In accordance with the present invention, the method for preparing a carbamate comprises (1) reacting (a) an aliphatic substituted urea and/or a derivative thereof having the general formula (I):

$$R^1R^2N\text{---}CO\text{---}NR^3R^4 \qquad (I)$$

wherein:
 $R^1$, $R^2$, $R^3$ and $R^4$ are each independently selected from the group consisting of a hydrogen atom, an aliphatic group or a derivative thereof, a cycloaliphatic group or a derivative thereof, and an araliphatic group or a derivative thereof;
with
(b) a hydroxyl group containing compound having the general formula (II):

$$R^5(OH)_n \qquad (II)$$

wherein:
 $R^5$ is independently selected from the group consisiting of an aliphatic group or a derivative thereof, a cycloaliphatic group or a derivative thereof, an araliphatic group or a derivative thereof, and an aromatic group or a derivative thereof,
 and
 n represents 1, 2, 3 or 4;
thereby forming a carbamate having the general formula (III):

$$(R^1R^2N\text{---}CO\text{---}O)_nR^5 \qquad (III)$$

wherein:
 $R^1$ and $R^2$ are each independently selected from the group consisting of a hydrogen atom, an aliphatic group or a derivative thereof, a cycloaliphatic group or a derivative thereof, and an araliphatic group or a derivative thereof,
 $R^5$ is independently selected from the group consisiting of aliphatic group or its derivatives, cycloaliphatic group or its derivatives, araliphatic group or its derivatives, and aromatic group or its derivatives,
 and
 n represents 1, 2, 3 or 4.

In a preferred embodiment, the relative amounts of the components present are such that the molar ratio of the hydroxyl group(s) present in (b) the hydroxyl group containing compound to (a) the aliphatic substituted urea and/or its derivatives ranges from 1:1 to 200:1.

Another objective of the present invention is to provide a catalyst which is suitable for promoting the carbamate reaction. In accordance with the present invention, the catalyst comprises a catalytically active component and a catalyst support, with the catalytically active component being carried by the catalyst support, and the catalytically active component comprises a transition metal oxide and/or a composite of transition metal oxides. Suitable transition metal oxides include those having the general formula $AO_x$, wherein A is a transition metal element. Suitable composites of transition metal oxides include those corresponding to one of the general formulas $AO_x\text{-}BO_y$ or $AO_x\text{-}BO_y\text{-}CO_z$, wherein in each formula A, B and C (if present) each independently represent a transition metal element; x, y and z each independently represent a number within the range of 0.5 to 4. In addition, in each formula, the transition metal element is selected from the group consisting of vanadium (i.e. V), chromium (i.e. Cr), molybdenum (i.e. Mo), tungsten (i.e. W), manganese (i.e. Mn), iron (i.e. Fe), nickel (i.e. Ni), palladium (i.e. Pd), platinum (i.e. Pt), copper (i.e. Cu), cadmium (i.e. Cd), mercury (i.e. Hg), titanium (i.e. Ti), lanthanum (i.e. La), cerium (i.e. Ce), neodymium (i.e. Nd), ytterbium (i.e. Yb), praseodymium (i.e. Pr), promethium (i.e. Pm), samarium (i.e. Sm), gadolinium (i.e. Gd), terbium (i.e. Tb), holmium (i.e. Ho), erbium (i.e. er), thulium (i.e. Tm) and lutetium (i.e. Lu).

Another object of this invention is to provide a method for preparing the above described catalyst. In accordance with the present invention, this method comprises (1) heating a catalyst support at a temperature of 100° C. to 1000° C.; (2) impregnating the catalyst support in a solution to obtain a catalyst precursor, in which the solution comprises a catalytically active component precursor with the catalytically active component precursor being selected from the group consisting of an anhydrous salt of a transition metal, a hydrous salt of a transition metal and an organic derivative of a transition metal, and in which the pH value of the solution is equal to or less than 8; and (3) calcinating the catalyst precursor to obtain a catalyst at the calcination temperature of 200° C. to 1000° C. In this embodiment, the transition metal element of the catalytically active component precursor is selected from the group consisting of vanadium (i.e. V), chromium (i.e. Cr), molybdenum (i.e. Mo), tungsten (i.e. W), manganese (i.e. Mn), iron (i.e. Fe), nickel (i.e. Ni), palladium (i.e. Pd), platinum (i.e. Pt), copper (i.e. Cu), cadmium (i.e. Cd), mercury (i.e. Hg), titanium (i.e. Ti), lanthanum (i.e. La), cerium (i.e. Ce), neodymium (i.e. Nd), ytterbium (i.e. Yb), praseodymium (i.e. Pr), promethium (i.e. Pm), samarium (i.e. Sm), gadolinium (i.e. Gd), terbium (i.e. Tb), holmium (i.e. Ho), erbium (i.e. er), thulium (i.e. Tm) and lutetium (i.e. Lu). .

This invention relates to a new method for preparing a carbamate, a suitable catalyst for this new method, a new catalyst, and the method for preparing the catalyst. In this new method for preparing a carbamate provided by the invention, a carbamate is obtained by reacting (a) an aliphatic substituted urea and/or its derivative with (b) a hydroxyl group containing compound. This reaction does not involve toxic carbon monoxide (i.e. CO), and the reaction conditions are relatively mild, with high catalytic activity and reaction selectivity of the catalyst, and a relatively short reaction time. Furthermore, the catalyst can be readily separated from the reaction system and recycled easily, which will facilitate scale up and industrial application.

DETAILED DESCRIPTION

The present invention provides a new method for preparing a carbamate comprising (1) reacting (a) an aliphatic substituted urea and/or its derivatives, with (b) a hydroxyl group containing compound to obtain a carbamate.

Compared to any methods for the preparation of a carbamate which are disclosed in the prior art, the present reaction between (a) an aliphatic substituted urea and/or its derivatives and (b) a hydroxyl group containing compound required by this invention possesses a particular high conversion rate and yield.

In particular, the present reaction is mild and efficient, when selecting dicyclohexyl substitute urea to react with a hydroxyl group containing compound to prepare a cyclohexyl carbamate.

This invention also provides a catalyst which is suitable for promoting the carbamate reaction in the new method. The new catalyst, which possesses high catalytic activity and reaction selectivity, can reduce the reaction time, as well as improve the conversion rate of the aliphatic substituted urea and/or its derivatives and the yield of the carbamate. Finally, the catalyst can be separated from the reaction system and recycled easily.

In particular, dicyclohexyl urea can be reacted with a hydroxyl group containing compound in the presence of the catalyst, to obtain a cyclohexyl carbamate. In this process, the conversion rate of the dicyclohexyl urea can be greater than or equal to 90%, the yield of the cyclohexyl carbamate can be greater than or equal to 85% after a separation process, and the purity of the obtained cyclohexyl carbamate can be greater than or equal to 98%.

The method for preparing a carbamate comprises (1) reacting (a) an aliphatic substituted urea and/or its derivatives having the general formula (I) as set forth herein, with (b) a hydroxyl group containing compound having the general formula (II) as set forth herein to obtain a carbamate having the general formula (III) as set forth herein, in accordance with the following equation:

$$n\ R^1R^2N\text{—}CO\text{—}NR^3R^4(I) + R^5(OH)_n(II) \rightarrow (R^1R^2N\text{—}CO\text{—}O)_nR^5(III) + n\ R^3R^4NH$$

wherein:

$R^1$, $R^2$, $R^3$ and $R^4$ are each independently selected from the group consisting of a hydrogen atom, an aliphatic group or a derivative thereof, a cycloaliphatic group or a derivative thereof, and an araliphatic group or a derivative thereof, $R^5$ is independently selected from the group consisting of an aliphatic group or a derivative thereof, a cycloaliphatic group or a derivative thereof, an araliphatic group or a derivative thereof, and an aromatic group or a derivative thereof, and n represents 1, 2, 3 or 4.

In accordance with the present invention, $R^1$, $R^2$, $R^3$, $R^4$ can be same, partly the same or different. For example, $R^1=R^2=R^3=R^4$, or $R^1=R^2=R^3 \neq R^4$, or $R^1=R^2=R^4 \neq R^3$, or $R^1=R^3=R^4 \neq R^2$, or $R^2=R^3=R^4 \neq R^1$, or $R^1=R^2 \neq R^3=R^4$, or $R^1=R^3 \neq R^2=R^4$, or $R^1=R^4 \neq R^2=R^3$, or $R^1 \neq R^2 \neq R^3 \neq R^4$.

Suitable aliphatic groups for $R^1$, $R^2$, $R^3$ and $R^4$ can be an unbranched or a branched, a saturated aliphatic or an unsaturated aliphatic group. The saturated aliphatic group can be selected from, but is not limited to, the group consisting of methyl, ethyl, 1-propyl, 2-propyl, 1-butyl, 2-butyl, t-butyl, pentyl or its isomers, hexyl or its isomers, and higher homologues of hexyl or their isomers. The unsaturated aliphatic group can be, but is not limited to, vinyl or propenyl.

The aliphatic derivatives can also be selected from a substituted aliphatic group comprising one or more atoms differing from carbon (i.e. C) and hydrogen (i.e. H), and the atom differing from C and H can be selected from, but are not limited to, the group consisting of nitrogen (i.e. N), oxygen (i.e.O), sulfur (i.e. S), phosphorus (i.e. P), silicon (i.e.Si), arsenic (i.e. As), fluorine (i.e. F), chlorine (i.e. Cl), bromine (i.e. Br) and iodine (i.e. I). Preferred atoms include fluorine (i.e. F), chlorine (i.e. Cl), bromine (i.e. Br) and iodine (i.e. I). The aliphatic group derivative can be selected from, but is not limited to, the group consisting of 2,2,2-trifluoro ethyl, 1,1,1,3,3,3-hexfluoro-2-propyl, 2-methoxy-1-ethyl or 2-ethoxy-1-ethyl.

The cycloaliphatic group can be an unbranched or a branched, saturated or unsaturated cycloaliphatic group. The saturated cycloaliphatic group can be, but is not limited to, cyclopentyl or cyclohexyl. The unsaturated cycloaliphatic group can be, but is not limited to, 3-cyclopentenyl or its isomers, or 3-cyclohexenyl or its isomers.

The cycloaliphatic group derivative can include one or more atoms differing from carbon (i.e. C) and hydrogen (i.e. H), and the atom differing from C and H can be selected from, but is not limited to, the group consisting of nitrogen (i.e. N), oxygen (i.e. O), sulfur (i.e. S), phosphorus (i.e. P), silicon (i.e.Si), arsenic (i.e. As), fluorine (i.e. F), chlorine (i.e. Cl), bromine (i.e. Br) and iodine (i.e. I). Preferred atoms include fluorine (i.e. F), chlorine (i.e. Cl), bromine (i.e. Br) and iodine (i.e. I). Preferred atoms include fluorine (i.e. F), chlorine (i.e. Cl), bromine (i.e. Br) and iodine (i.e. I). The cycloaliphatic group derivative can be, but is not limited to, 4-chlorocyclohexyl, 4-chloromethyl-cyclohexyl or 4-methoxy-cyclohexyl.

The araliphatic group can be an unbranched or a branched, substituted saturated araliphatic group or substituted unsaturated araliphatic group. The substituted saturated araliphatic group can be selected from, but is not limited to, the group consisting of benzyl, 1-phenyl ethyl or 2-phenyl ethyl. The substituted unsaturated araliphatic group can be, but is not limited to, 3-phenyl-2-propenyl or its isomers.

The aromatic group derivative can include a substituted group comprising one or more atoms differing from carbon (i.e. C) and hydrogen (i.e. H). The atom differing from C and H can be selected from, but is not limited to, nitrogen (i.e. N), oxygen (i.e. O), sulfur (i.e. S), phosphorus (i.e. P), silicon (i.e. Si), arsenic (i.e. As), fluorine (i.e. F), chlorine (i.e. Cl), bromine (i.e. Br) and iodine (i.e. I). Preferred atoms include fluorine (i.e. F), chlorine (i.e. Cl), bromine (i.e. Br) and iodine (i.e. I). Preferred atoms include fluorine (i.e. F), chlorine (i.e. Cl), bromine (i.e. Br) and iodine (i.e. I). The aromatic group derivative can be selected from, but is not limited to, 4-chloro-benzyl, 4-chloro-phenyl ethyl or 4-methoxy-benzyl.

The aromatic group can be an unsubstituted aromatic group. For example, the aromatic group can be, but is not limited to, phenyl, naphthyl or anthryl.

The aromatic group derivative can be a substituted aromatic group. The substituted aromatic group can be substituted by one or more atoms differing from carbon (i.e. C) and hydrogen (i.e. H). The atom differing from C and H can be selected from, but is not limited to, the group consisting of nitrogen (i.e. N), oxygen (i.e. O), sulfur (i.e. S), phosphorus (i.e. P), silicon (i.e. Si), arsenic (i.e. As), fluorine (i.e. F), chlorine (i.e. Cl), bromine (i.e. Br) and iodine (i.e. I). Preferred atoms include fluorine (i.e. F), chlorine (i.e. Cl), bromine (i.e. Br) and iodine (i.e. I). Preferred atoms include fluorine (i.e. F), chlorine (i.e. Cl), bromine (i.e. Br) and iodine (i.e. I). The aromatic group derivative can be selected from, but is not limited to, methylphenyl, methoxyphenyl or nitrophenyl.

In a most preferred embodiment, the aliphatic substituted urea is dicyclohexyl urea.

The aliphatic substituted urea and/or its derivatives, can also be selected from industrial purity raw material, in which preferably, the purity is 98-100%.

The hydroxyl group containing compound can be selected from, but is not limited to, a monohydric alcohol, dihydric alcohol, trihydric alcohol and tetrahydric alcohol, with a monohydric alcohol being preferred. Suitable monohydric alcohols can be selected from unbranched or branched, saturated or unsaturated aliphatic alcohols. The saturated aliphatic alcohol can be selected from, but is not limited to, methanol, ethanol, 1-propanol, 2-propanol, 1-butanol, 2-butanol, tert-butanolj, pentanol or its isomers, hexanol or its isomers or their higher homologues. The unsaturated aliphatic alcohol can be selected from, but is not limited to, 1-hydroxy-propylene or its isomers, 1-hydroxy-2-butylene or its isomers or their higher homologues.

The amount of the raw materials which are preferably employed for the reaction is such that there is at least 1 mole of hydroxyl group present from (b) the hydroxyl group containing compound or the mixture of hydroxyl group containing compounds for each mole of (a) substituted urea. Preferably, there are at least 4 moles of hydroxyl groups from (b) the hydroxyl group containing compound or the mixture of hydroxyl group containing compounds present for each mole of (a) substituted urea. More preferably, there are at least 8 moles of hydroxyl groups from the hydroxyl group containing compound or the mixture of hydroxyl group containing compounds present for each mole of (a) substituted urea. There is no upper limit for the amount of (b) the hydroxyl group containing compound or the mixture of hydroxyl group containing compound present for each mole of (a) substituted urea. From an economical perspective, however, the upper limit should not exceed 200 moles, preferably 25 moles, of hydroxyl groups from the hydroxyl group containing compound or the mixture of hydroxyl group containing compounds present for each mole of (a) substituted urea.

The reaction can be carried out in a fixed bed, fluidized bed or slurry reactor.

In the reaction, it is possible to add any solvent which is inert under the reaction conditions. Suitable solvents to be mentioned can be preferably selected from, but are not limited to, aliphatic hydrocarbons, aromatic hydrocarbons, halogenated aromatic hydrocarbons, halogenated aliphatic hydrocarbons or ionic liquids.

The reaction can be carried out continuously, semi-continuously or batch-wise. There is no limit for the order of the addition of the raw materials and/or the catalyst, and the best way and/or most advantageous order can be readily determined in orienting experiments. Furthermore, it may be advantageous to remove the amine which is formed during the reaction from the reactor by appropriate means, either continuously or intermittently, to shift the reaction equilibrium to the product side.

The reaction temperature shall be suitable for the carbamate forming reaction. If the reaction temperature is too low, it will result in a huge decrease of the reaction rate, and if the reaction temperature is too high, the risk of reduced yield or selectivity due to unwanted side reactions will significantly increase. Thus, the reaction temperature is preferably selected to be in the range of, but is not limited to, 100° C. to 300° C., more preferably 120° C. to 280° C., and most preferably 160° C. to 240° C.

The reaction pressure is the autogenous pressure which develops at the chosen reaction temperature. Alternatively, the pressure can also be modified by adding an inert gas, in which the inert gas can be selected from, but is not limited to, nitrogen, a noble gas, carbon dioxide, or any other gases which are inert under the reaction condition, or mixtures of two or more of the aforementioned inert gases. The reaction pressure can be in the range of, but is not limited to, 0.1 to 6 MPa, preferably 0.1 to 5.5 MPa, more preferably 0.2 to 5.0 MPa.

The reaction time depends on reaction conditions. The reaction time can be selected from the range of, but is not limited to, less than or equal to 30 hours, preferably less than or equal to 18 hours, more preferably 2 to 15 hours, and most preferably 6 to 12 hours.

After the reaction is completed, the reaction mixture is removed from the reactor, separated and purified by distillation, crystallization, filtration, sedimentation, centrifugation, extraction, separation applying a membrane process, or other means or by combination of two or more of the aforesaid techniques/means.

The active component of the catalyst provided in the present invention is a transition metal oxide or a composite of a transition metal oxide. Suitable transition metal oxides include those having the general formula $AO_x$, in which A is a transition metal element, and x represents a number in the range of 0.5 to 4. Suitable composites of transition metal oxides include those corresponding to one or the general formulas: $AO_x$-$BO_y$ or $AO_x$-$BO_y$-$CO_z$, in which A, B and C (if present) each independently represent a transition metal element, and x, y and z (if present) each independently represent a number in the range of 0.5 to 4. Suitable transition metal elements for the transition metal oxides and/or compositions of transition metal oxides of the active component are selected from the group consisting of vanadium (i.e. V), chromium (i.e. Cr), molybdenum (i.e. Mo), tungsten (i.e. W), manganese (i.e. Mn), iron (i.e. Fe), nickel (i.e. Ni), palladium (i.e. Pd), platinum (i.e. Pt), copper (i.e. Cu), cadmium (i.e. Cd), mercury (i.e. Hg), titanium (i.e. Ti), lanthanum (i.e. La), cerium (i.e. Ce), neodymium (i.e. Nd), ytterbium (i.e. Yb), praseodymium (i.e. Pr), promethium (i.e. Pm), samarium (i.e. Sm), gadolinium (i.e. Gd), terbium (i.e. Tb), holmium (i.e. Ho), erbium (i.e. er), thulium (i.e. Tm) and lutetium (i.e. Lu). Preferred transition metal elements include titanium, molybdenum, tungsten, iron, nickel, lanthanum, cerium, neodymium or ytterbium. More preferred are titanium, lanthanum and cerium.

Typical examples of the transition metal oxide include, but are not limited to, $LaO_x$, $CeO_y$ or $TiO_z$, wherein x, y, z are each in the range of 0.5 to 4.

A typical example of the transition metal oxide composites is $LaO_x$—$CeO_y$—$TiO_z$, wherein x, y, z are each in the range of 0.5 to 4.

The catalyst support of the catalyst of the present invention includes all the support materials known in the art. The catalyst support can be selected from, for example, silica gel, alumina, $SnO_2$, $TiO_2$, $SiO_2$, $MgO$, $Fe_2O_3$, $ZnO$ and $ZrO_2$.

Suitable examples of the catalyst include $LaO_x$—$TiO_z$/$SiO_2$ (in which the active component is $LaO_x$—$TiO_z$ and the catalyst support is $SiO_2$) or $LaO_x$—$CeO_y$—$TiO_z$/$SiO_2$ (in which the active component is $LaO_x$—$CeO_y$—$TiO_z$ and the support is $SiO_2$).

There is no special limitation with regard to the shape of the catalyst support. Typical examples of the suitable shapes are spheres, cylindrical or irregular.

There is also no special limitation with regard to the average diameter of the catalyst support. Suitable average diameters of the catalyst support can be selected from the range of, but is not limited to, 0.01 to 10 mm, preferably 1 to 5 mm, and more preferably 1 to 3 mm.

A special limitation is not present with regard to the pore volume of the catalyst support. A suitable pore volume of the catalyst support can be selected from the range of, but is not limited to, 0.01 to 2 ml/g, preferably 0.01 to 1 ml/g, more preferably 0.1 to 0.8 ml/g, and most preferably 0.2 to 0.6 ml/g.

A special limitation does not exist with regard to the BET surface of the catalyst particles. Suitable examples for the BET surface of the support particles can be selected from the range of, but is not limited to, 1 to 2000 m²/g, preferably 100 to 1500 m²/g, more preferably 200 to 1000 m²/g, and most preferably 400 to 1000 m²/g.

The amount of the catalytically active component can be selected from the range of, but is not limited to, 0 to 30 wt %, and preferably 4 to 20 wt. %, based on 100 wt. % of the catalyst.

The method for preparing the catalyst for the reaction of synthesizing carbamate as set forth in the present invention comprises the steps of heating, impregnating and calcinating. More specifically, the process comprises (1) heating the catalyst support to 100 to 1000° C., (2) impregnating the catalyst support in solution to obtain a catalyst precursor, in which the solution comprises a catalytically active precursor component, and the pH of the solution is less than or equal to 8; and (3) calcinating the catalyst precursor to obtain a catalyst at the calcination temperature of 200 to 1000° C. Suitable catalytically active precursor components are selected from the group consisting of an anhydrous salt of a transition metal, a hydrous salt of a transition metal and an organic derivative of a transition metal, with the transition metal element being selected from the group consisting of: vanadium, chromium, molybdenum, tungsten, manganese, iron, nickel, palladium, platinum, copper, cadmium, mercury, titanium, lanthanum, cerium, neodymium, ytterbium, praseodymium, promethium, samarium, gadolinium, terbium, holmium, erbium, thulium and lutetium.

In accordance with the present invention, this method can further include a drying step after the impregnating step and before the calcinating step. Suitable drying temperatures are selected from the range of, but are not limited to, 0 to 120° C., preferably 40 to 110° C., and more preferably 60 to 100° C. The time of the drying step is less than or equal to 24 hours, preferably less than or equal to 15 hours, and more preferably from 4 to 10 hours.

The catalyst support is heated at 100 to 1000° C., preferably 300 to 900° C., and more preferably 400 to 700° C. The heating time is less than or equal to 24 hours, preferably less than or equal to 10 hours, and more preferably 1 to 6 hours. There is no special limitation with regard to the pressure of the heating step. The preferred pressure of the heating step is atmospheric pressure. The atmosphere of the heating step is air, oxygen or nitrogen, preferably air or oxygen, more preferably air.

In the impregnating step, the catalyst support treated by heating step is impregnated using a solution that comprising a catalytically active component precursor. The catalytically active component precursor includes one or more anhydrous or hydrous salts and/or organic derivatives of the transition metals. The transition metal can be selected from the group consisting of, but is not limited to, V, Cr, Mo, W, Mn, Fe, Ni, Pd, Pt, Cu, Cd, Hg, Ti, La, Ce, Nd, Yb, Pr, Pm, Sm, Gd, Tb, Ho, Er, Tm and Lu. It is preferred for the transition metal to be selected from the group consisting of Ti, Mo, W, Fe, Ni, La, Ce, Nd or Yb, and more preferably from the group consisting of Ti, La or Ce.

The solvent can be selected from, but is not limited to, water, an alcohol, an ester, and preferably water.

Some suitable examples of the catalytically active component precursor include, but are not limited to, halide of transition metal, hydroxide of transition metal, nitrate of transition metal, sulfate of transition metal, acetate of transition metal and their mixtures, and preferably nitrates of transition metal. More specifically, the catalytically active component precursor may be $La(NO_3)_3 \cdot 6H_2O$ or $Ce(NO3)3 \cdot 6H_2O$. The, organic derivatives of transition metal can be selected from, but is not limited to, the corresponding alkoxides of the transition metal, with a typical example being tetrabutyl titanate. The total concentration of the catalytically active component precursor is less than or equal to 40 wt. %, based on 100 wt. % of the solution of the catalytically active component precursor.

The pH value of the solution of the catalytically active component precursor is less than or equal to 8, preferably less than or equal to 7, most preferably from 1 to 4. The pH value of the solution can be adjusted by addition of aqueous or non-aqueous acids. The aqueous or non-aqueous acids can be selected from, but are not limited to, HCl, $HNO_3$, $H_2SO_4$, $H_3PO_4$ or $CH_3COOH$.

There is no special limit with regard to the temperature of the impregnating step, and preferably the temperature of the impregnating step is room temperature. The time of the impregnating step is less than or equal to 24 hours, preferably from 2 to 20 hours.

The temperature of the calcinating step should be high enough to transform the catalyst precursor into the catalyst, and is preferably in the range of 200 to 1000° C., and more preferably in the range of 300 to 700° C. There is no special limitation with regard to the time of the calcinating step, preferably the time of the calcinating step is 1 to 20 hours, and more preferably 2 to 10 hours.

The calcinating step can be carried out either in an inert atmosphere or in an oxidizing atmosphere. The inert atmosphere can be selected from, but is not limited to, $N_2$, a noble gas, a non-oxidative gas, a non-reducing gas, or a mixture of two or more of the aforementioned gases, preferably $N_2$. The oxidizing atmosphere can be selected from, but is not limited to, oxygen or gases containing oxygen, preferably air.

In the reaction for preparing the carbamate, there is no special limit with regard to the amount of catalyst. Preferably the weight ratio between the catalyst and the aliphatic substituted urea and/or its derivatives is equal to or less than 1:1, and more preferably 0.01:1 to 0.3:1.

The catalyst can be separated from the reaction system and recycled easily. For example, the catalyst can be separated from the reaction mixture and recycled by distillation, crystallization, filtration, sedimentation, centrifugation, extraction, membrane separation, or other proper techniques/means, or by a combination of two or more of the aforesaid techniques/means.

After being separated from the reaction system, and without any further treatment, the catalyst can be directly recycled, or recycled after reactivation/regeneration by ways of washing in an appropriate solvent, filtration, evaporating, centrifugation, drying, calcination or by a combination of two or more of the aforesaid techniques/means.

After being separated from the reaction product, without being separated from the catalyst, the remaining reaction mixture which comprises un-reacted raw materials, catalyst, intermediates and solvents can be recycled by addition into the new reaction process directly.

The following examples further illustrate details for the process of this invention. The invention, which is set forth in the foregoing disclosure, is not to be limited either in spirit or scope by these examples. Those skilled in the art will readily understand that known variations of the conditions of the following procedures can be used. Unless otherwise noted, all temperatures are degrees Celsius and all percentages are percentages by weight.

EXAMPLES

The reactor of the reaction for preparing a carbamate can be selected from, but is not limited to, a stirred reactor or a tubular reactor, and the tubular reactor can be selected from a tubular reactor with or without insert, a tubular reactor with or without mixing element, a tubular reactor with or without redispersing element, or a combination of two or more of the aforesaid tubular reactors.

The catalyst support used in the following examples is $SiO_2$ particle, and this particular $SiO_2$ particle is commercially available. The basic properties of the $SiO_2$ particle are:
  pore volume of 0.35 to 0.45 ml/g,
  average pore diameter of 2 to 3 nm,
  BET surface of 750 to 800 $m^2/g$,
  average diameter of 1 to 2 mm,
  bulk density of 720 g/l,
  and specific heat of 0.92 KJ/kg° C.
Preparation of the Catalyst:

Example 1

5.0 ml $C_{16}H_{36}O_4Ti$ ($Ti(OBu)_4$) was dropwise added into a 100 ml beaker containing 10 ml 65 to 68 wt. % aqueous $HNO_3$ to adjust the pH value of the resulting solution to 1 to 2. Then 20 g $SiO_2$ support heated at 600° C. in the air atmosphere for 2 hours was added into the solution and impregnated at room temperature for 4 hours to obtain a catalyst precursor. The resulting catalyst precursor was dried at 100° C. in the air atmosphere for 4 hours and then calcined at 600° C. for 4 hours to obtain a catalyst A. The catalytically active component precursor of the catalyst A was $TiO_2$, and the catalyst support was $SiO_2$, and the catalyst A comprised 6.0 wt. % $TiO_2$.

Example 2

2.5 ml $C_{16}H_{36}O_4Ti$ ($Ti(OBu)_4$) was dropwise added into a 100 ml beaker containing 2.1 g $La(NO_3)_3 \cdot 6H_2O$, 1.0 g $Ce(NO_3)_3 \cdot 6H_2O$, and 5 ml 65 to 68 wt. % aqueous $HNO_3$ to adjust the pH value of the resulting solution to 1 to 2. Then 20 g $SiO_2$ support heated at 600° C. in the air atmosphere for 2 hours was added into the solution and impregnated at room temperature for 10 hours to obtain a catalyst precursor. The resulting catalyst precursor was dried at 100° C. in the air atmosphere for 4 hours and then calcined at 600° C. for 4 hours to obtain a catalyst B. The catalytically active component precursor of the catalyst B was $LaO_x$—$CeO_y$—$TiO_2$, and the catalyst support was $SiO_2$, and the catalyst B comprised 4.0 wt. % $LaO_x$, 2.0 wt. % $CeO_y$, 3.0 wt. % $TiO_2$.

Example 3

2.5 ml $C_{16}H_{36}O_4Ti$ ($Ti(OBu)_4$) was dropwise added into a 100 ml beaker containing 1.1 g $La(NO_3)_3 \cdot 6H_2O$, 2.0 g $Ce(NO_3)_3 \cdot 6H_2O$, and 5 ml 65 to 68 wt. % aqueous $HNO_3$ to adjust the pH value of the resulting solution to 1 to 2. Then 20 g $SiO_2$ support heated at 600° C. in the air atmosphere for 2 hours was added into the solution and impregnated at room temperature for 10 hours to obtain a catalyst precursor. The resulting catalyst precursor was dried at 100° C. in the air atmosphere for 4 hours and then calcined at 600° C. for 4 hours to obtain a catalyst C. The catalytically active component precursor of the catalyst C is $LaO_x$—$CeO_y$—$TiO_2$, and the catalyst support was $SiO_2$, and the catalyst C comprised 2.0 wt. % $LaO_x$, 4.0 wt. % $CeO_y$, 3.0 wt. % $TiO_2$.
Preparation of the Carbamate:
  Quantitative analysis of the organic carbamate was conducted by GC using an external standard method. An Agilent 1790 GC was used, that was equipped with a 30 m×0.25 mm×0.33 μm capillary column and FID detector.

Qualitative analyses of other possible by-products are conducted using a HP 6890/5973 GC-MS equipped with a 30 m×0.25 mm×0.33 μm capillary column and with a chemstation containing a NIST Mass Spectral Database.

Example 4

20 ml methanol, 0.8 g dicyclohexyl urea (DCU) and 0.2 g catalyst A, B or C, respectively, were successively added into a 45 ml stainless steel reactor equipped with a magnetic stirrer and a gas releasing valve. The reactor was sealed and heated to 210° C., and reacted at 210° C. for 10 hours, and the reaction pressure was about 3 MPa. After the reaction was finished, the reactor was cooled down to room temperature. The catalyst could be filtrated. Raw methyl cyclohexyl carbamate (MCC) was obtained as a solid after the solution containing methanol and desired product was distilled at 60° C. to remove excess methanol. The obtained raw MCC was dissolved in 120 ml diethyl ether and filtrated to remove the possible residual dicyclohexyl urea. The diethyl ether was removed from the solution at 60° C. MCC was obtained as a white solid, the purity of the MCC was more than or equal to 98%. The results obtained were shown in Table 1.

TABLE 1

MCC obtained by reacting methanol with dicyclohexyl urea (DCU) in the presence of catalyst

| Catalyst | DCU conversion | MCC GC yield | MCC isolated yield |
|---|---|---|---|
| A | 96 wt % | 95 wt % | 87 wt % |
| B | 99 wt % | 98 wt % | 89 wt % |
| C | 93 wt % | 90 wt % | 85 wt % |

Example 5

20 ml ethanol, 1.0 g dicyclohexyl urea (DCU) and 0.2 g catalyst A, B or C, respectively, were successively added into a 45 ml stainless steel reactor equipped with a magnetic stirrer and a gas releasing valve. The reactor was sealed and heated to 210° C., and reacted at 210° C. for 10 hours, and the reaction pressure was about 1.5 MPa. After the reaction was finished, the reactor was cooled down to room temperature. The catalyst could be filtrated. Raw ethyl cyclohexyl carbamate (ECC) was obtained as a solid after the solution containing ethanol and desired product was distilled at 70° C. to remove excess ethanol. The obtained raw ECC was dissolved in 120 ml diethyl ether and filtrated to remove the possible residual dicyclohexyl urea. The diethyl ether was removed from the solution at 60° C. ECC was obtained as a white solid, and the purity of the ECC was more than or equal to 98%. The results obtained were shown in Table 2.

TABLE 2

ECC obtained by reacting ethanol with dicyclohexyl urea (DCU) in the presence of catalyst

| Catalyst | DCU conversion | ECC GC yield | ECC isolated yield |
|---|---|---|---|
| A | 97 wt % | 96 wt % | 88 wt % |
| B | 99 wt % | 98 wt % | 90 wt % |
| C | 94 wt % | 93 wt % | 86 wt % |

Example 6

20 ml butanol, 1.5 g dicyclohexyl urea (DCU) and 0.2 g catalyst A, B or C, respectively, were successively added into a 45 ml stainless steel reactor equipped with a magnetic stirrer and a gas releasing valve. The reactor was sealed and heated to 210° C., and reacted at 210° C. for 10 hours, and the reaction pressure was about 0.5 MPa. After the reaction was finished, the reactor was cooled down to room temperature. The catalyst could be filtrated. Raw butyl cyclohexyl carbamate (BCC) was obtained as a solid after the solution containing butanol and desired product was distilled at 70° C. to remove excess butanol. The obtained raw BCC was dissolved in 120 ml diethyl ether and filtrated to remove the possible residual dicyclohexyl urea. The diethyl ether was removed from the solution at 60° C. BCC was obtained as a white solid, the purity of the BCC was more than or equal to 98%. The results obtained were shown in Table 3.

TABLE 3

BCC obtained by reacting butanol with dicyclohexyl urea (DCU) in the presence of catalyst

| Catalyst | DCU conversion | BCC GC yield | BCC isolated yield |
|---|---|---|---|
| A | 96 wt % | 95 wt % | 89 wt % |
| B | 99 wt % | 98 wt % | 92 wt % |
| C | 93 wt % | 92 wt % | 85 wt % |
| B[a] | 95 wt % | 94 wt % | 90 wt % |

[a]the catalyst was recycled for the fourth time and used in this example

Although the present invention is illustrated by the examples, it is not limited by these examples in any way. Without departing from the spirit and scope of this invention, those skilled in the art can make any modifications and alternatives. And the protection of this invention is based on the scope defined by the claims of this application.

What is claimed is:

1. A method for preparing a carbamate, comprising (1) reacting
   (a) an aliphatic substituted urea and/or a derivative thereof having the general formula (I):

$$R^1R^2N\text{—}CO\text{—}NR^3R^4 \qquad (I)$$

wherein:
   $R^1$, $R^2$, $R^3$ and $R^4$ are each independently selected from the group consisting of a hydrogen atom, an aliphatic group or a derivative thereof, a cycloaliphatic group or a derivative thereof, and an araliphatic group or a derivative thereof;
   with
   (b) a hydroxyl group containing compound having the general formula (II):

$$R^5(OH)_n \qquad (II)$$

wherein:
   $R^5$ is independently selected from the group consisting of an aliphatic group or a derivative thereof, a cycloaliphatic group or a derivative thereof, an araliphatic group or a derivative thereof, and an aromatic group or a derivative thereof, and
   n represents 1, 2, 3 or 4;
   in the presence of
   (c) a catalyst comprising a catalytically active component and a catalyst support with said catalytically acid component being carried by said catalyst support, wherein said catalytically active component comprises a transition metal oxide and/or a composite of a transition metal oxide, wherein:

(i) said transition metal oxide corresponds to the general formula:

$AO_x$, wherein:
A is a transition metal element, and
x represents a number within the range of 0.5 to 40;
(ii) said cormposite of a transition metal oxide corresponds to one of the general formulas:

$AO_x—BO_y$ or $AO_x—BO_y—CO_z$, wherein in each formula:
A, B and C each independently represent a transition metal element, and
x, y and z each independently represent a number within the range of 0.5-4;
wherein said transition metal element is selected from the group consisting of vanadium, chromium, molybdenum, tungsten, manganese, iron, nickel palladium, patinum, copper, cadmium, mercury, titanium, lanthanum, cerium, neodynium, ytterbium, praseodymium, promethium, samarium, gadolinium, terbium, holmium, erbium, thulium and lutetium;
and wherein said catalyst support:
(i) comprises a material which is selected from the group consisting of silica gel, $Al_2O_3$, $SnO_2$, $TiO_2$, MgO, ZnO, $ZrO_2$ and $SiO_2$,
(ii) the average diameter of said catalyst support ranges from 0.01-10 mm,
(iii) the pore volume of said catalyst support ranges from 0.01-2 ml/g, and
(iv) the specific surface area of said catalyst support ranges from 1 to 2000 $m^2$/g;

thereby forming a carbamate having the general formula (III):

$(R^1R^2N—CO—O)_nR^5$     (III)

wherein:
$R^1$ and $R^2$ are each independently selected from the group consisting of a hydrogen atom, an aliphatic group or a derivative thereof, a cycloaliphatic group or a derivative thereof, and an araliphatic group or a derivative thereof,
$R^5$ is independently selected from the group consisiting of aliphatic group or its derivatives, cycloaliphatic group or its derivatives, araliphatic group or its derivatives, and aromatic group or its derivatives, and
n represents 1, 2, 3 or 4.

2. The method of claim 1, wherein (a) said aliphatic substituted urea comprises dicyclohexyl urea.

3. The method of claim 1, wherein the molar ratio of the hydroxyl groups present in (b) said hydroxyl group containing compound to (a) said aliphatic substituted urea and/or derivatives thereof ranges from 1:1 to 200:1.

4. The method of claim 3, wherein, the molar ratio of the hydroxyl group present in (b) said hydroxyl group containing compound to (a) said aliphatic substituted urea and/or derivatives thereof ranges from 1:1 to 4:1.

5. The method of claim 1, wherein the reaction temperature ranges from 100 to 300° C.

6. The method of claim 5, wherein the reaction temperature ranges from 160 to 240° C.

7. The method of claim 1, wherein said transition metal element is selected from the group consisting of titanium, lanthanum and cerium.

8. The method of claim 1, wherein, the weight ratio between said catalyst and said aliphatic substituted urea is equal to or less than 1:1.

9. The method of claim 8 wherein, the weight ratio between said catalyst and said aliphatic substituted urea ranges from 0.01:1 to 0.3:1.

* * * * *